US005466783A

United States Patent [19]

Wun et al.

[11] Patent Number: 5,466,783
[45] Date of Patent: Nov. 14, 1995

[54] HUMAN TISSUE FACTOR INHIBITOR

[75] Inventors: Tze-Chein Wun, St. Louis; Kuniko K. Kretzmer, Eureka; George J. Broze, Jr., St. Louis, all of Mo.

[73] Assignees: Monsanto Company; Washington University, both of St. Louis, Mo.

[21] Appl. No.: 93,285

[22] Filed: Jul. 15, 1993

Related U.S. Application Data

[60] Continuation of Ser. No. 566,280, Aug. 13, 1990, abandoned, which is a division of Ser. No. 123,753, Nov. 23, 1987, Pat. No. 4,966,852, which is a continuation-in-part of Ser. No. 77,366, Jul. 23, 1987, abandoned.

[51] Int. Cl.$^6$ .................................................. C07K 13/00
[52] U.S. Cl. ........................... 530/380; 530/350; 530/395
[58] Field of Search ........................... 530/350, 395, 530/399, 380

[56] References Cited

U.S. PATENT DOCUMENTS

| | | | |
|---|---|---|---|
| 4,393,133 | 7/1983 | Knowles et al. | 435/6 |
| 4,495,280 | 1/1985 | Bujard et al. | 435/6 |
| 4,788,135 | 11/1988 | Davis et al. | 435/6 |
| 4,966,852 | 10/1990 | Wun et al. | 435/235 |
| 5,106,833 | 4/1992 | Broze, Jr. et al. | 514/12 |
| 5,219,994 | 6/1993 | Buonassisi et al. | 530/380 |
| 5,312,736 | 5/1994 | Rasmussen et al. | 435/69.2 |

OTHER PUBLICATIONS

Kondo et al., Thromb. Res. 48(4), 449–59 (1987) CA 108, 53419y.
Nakajima et al., Ketsuaki to Mykkan 19(2), 202–4 (1988) CA 109, 183243t.
Chem. Abs. vol. 100, No. 3, 20976, (1983), Smariga et al.
Smariga et al. *Biochimica et Biophysica Acta* 761:109–118 (1983).
Hjort *Scand J. Clin Lab Invest* 9(27):76–97 (1957).
Sofer et al. *Bio/Techniques* 1(4):198–203 (1983).
Broze and Miletich, Blood 69, 150–155 (1987).
Broze and Miletich, Proc. Natl. Acad. Sci. USA 84, 1886–1890 (1987).
Sanders et al., Blood 66, 204–212 (1985).
Rapaport, Blood 73, 359–365 (1989).
Kaumeyer et al., Nucleic Acids Res. 14(20), 7839–7850 (1986).
Hochstrasser & Wachter, Hoppe–Seyler's Z. Physiol. Chem. 364, 1679–1687 (1983).
Broze and Miletich, "Characterization of Tissue Factor in Serum", American Heart Assn. Absts. Nov. 19, 1986.
Bourguignon et al., Bioch. Biophys. res. Commun., 131(3), 1146–53 (1985).
Salier et al., Proc. Natl. Acad. Sci. USA, 84, 8272–8276 (1987).
Warn–Cramer, Thrombosis Res. 48, 11–22 (1987).
Kikutani et al., Cell 47, 657–665 (1986).
Warn–Cramer et al. "Partial Purification of a Factor X–Dependent Plasma Inhibitor of the Factor VII/a Tissue Factor Complex", Amer. Heart Assoc. Program Lecture, Dallas, Tex., Nov. 19, 1986.
Lackner et al., Nucleic Acids Res. 13(12), 4597–4608, (1985).
Carson, S. D., The Journal of Biological Chemistry, 262(2), 718–21 (1987).
Rao et al., Blood 69(2), 645–51 (1987) CA 106, 100036s.
Bajaj et al., J. Clin. Invest. 79(6), 874–78 (1987) CA 107, 213856y.
Hubbard et al., Throm. Res. 46(4), 527–37 (1987) CA 107, 37214b.

*Primary Examiner*—Garnette D. Draper
*Assistant Examiner*—Shelly Guest Cermak
*Attorney, Agent, or Firm*—Scott J. Meyer

[57] ABSTRACT

A cDNA clone having a base sequence for human tissue factor inhibitor (TFI) has been developed and characterized and the amino acid sequence of the TFI has been determined.

2 Claims, 8 Drawing Sheets

FIG.3A

```
  1  GGC GGG TCT GCT TCT AAA AGA AGT AGA GAA GAT AAA TCC TGT CTT CAA TAC CTG GAA GGA AAA ACA AAA TAA CCT CAA CTC CCT TTT           16
                                                                                                      +1  Met Ile Tyr Thr Met Lys Val His Ala Leu Trp Ala Leu Ser Val Cys

91  GAA AAA AAC CCA AGA ACT TTC ATC AGA GAT TTT ACT TAC ATG ATT TAC ACA ATG AAG AAA GTA CAT GCA CTT TGG GCT CTT GTA TGC           46
     Ile Tyr Thr Met Lys Lys Val His Ala Leu Trp Ala Leu Ser Val Cys Glu Lys Asn Pro Arg Thr Phe Ile Arg Asp Phe Thr Tyr Met

181  CTG CTG CTT AAT CTT GCC CCT GCC CCT GAT TCT GAG GAA GAT GAA CAC ATT ATC ACA GAT GAA GAG TTG CCA CCA ATT TTC ACT               76
     Leu Leu Leu Asn Leu Ala Pro Ala Pro Asp Ser Glu Glu Asp Glu His Thr Ile Ile Thr Asp Glu Glu Leu Pro Pro Ile Phe Thr

271  CTG AAA CTT ATG CAT TCA TTT TGT GCA TTC AAG GCG GAT GAT GGC CCA TGT AAA GCA ATC ATG AAA AGA TTT TTC TTC AAT ATT TTC ACT      106
     Leu Lys Leu Met His Ser Phe Cys Ala Phe Lys Ala Asp Asp Gly Pro Cys Lys Ala Ile Met Lys Arg Phe Phe Phe Asn Ile Phe Thr

361  CGA CAG TGC GAA GAA TTT ATA TAT GGC ATT ATA AAG ACA ATT GAA AGT CTG GAA GAG TGC AAA AAA ATG TGT GGA ATA TGT CGA AGA          135
     Arg Gln Cys Glu Glu Phe Ile Tyr Gly Ile Ile Lys Thr Ile Glu Ser Leu Glu Glu Cys Lys Lys Met Cys Gly Ile Cys Arg Gly

451  GAT AAT GCA AAC AGG ATT AAC ACA TTG CAA GAA ACA CCA AAG GAA CAA ATC AGA CGA TTC TGC TTT TGC AAG TAT GGA TGC CTG GGC AAT ATG   166
     Asp Asn Ala Asn Arg Ile Asn Thr Leu Gln Glu Thr Pro Lys Glu Gln Ile Arg Arg Phe Cys Phe Cys Lys Tyr Gly Cys Leu Gly Asn Met

541  TAT ATT ACC AGG TAT TTT TAT AAC CAG AAA ATT CAG TGT GAA CGT TTC AAG TAT CGT TTC CAG GTG GAT AAT TAT ACC CAG CTC AAT GCT GTG AAT AAC  196
     Tyr Ile Thr Arg Tyr Phe Tyr Asn Gln Lys Ile Gln Cys Glu Arg Phe Lys Tyr Arg Phe Gln Val Asp Asn Tyr Thr Gln Leu Asn Ala Val Asn Asn

631  ACA CTC GAA GAA TGC AAG AAC ATT TGT GAA GAT GGT CCC AAT GGT TTC CAG GTG GAT AAT TAT ACC CAG CTC AAT GCT GTG AAT AAC           196
     Thr Leu Glu Glu Cys Lys Asn Ile Cys Glu Asp Gly Pro Asn Gly Phe Gln Val Asp Asn Tyr Gly Thr Gln Leu Asn Ala Val Asn Asn

721  TCC CTG ACT CCG CAA TCA ACC AAG GTT CCC AGC CTT GAA TTT CAC GGT GCC TCA TGG TGT CTC ACT CCA GAC AGA GGA TTG TGT                226
     Ser Leu Thr Pro Gln Ser Thr Lys Val Pro Ser Leu Glu Phe His Gly Pro Ser Leu Thr Pro Asp Arg Gly Leu Cys

811  CGT GCC AAT GAG AAC AGA TTC TAC TAC TCA ATT GGG AAA TGC CGC ATT AAG TAC AGT GGA TGT GGG GGA AAT GAA AAC AAT                   256
     Arg Ala Asn Glu Asn Arg Phe Tyr Tyr Ser Ile Gly Lys Cys Arg Pro Phe Lys Tyr Ser Gly Cys Gly Gly Asn Glu Asn Asn
```

```
901  TTT ACT TCC AAA CAA GAA TGT CTG AGG GCA TGT AAA AAA GGT TTC ATC CAA AGA ATA TCA AAA GGA GGC CTA ATT AAA ACC AAA AGA AAA
     Phe Thr Ser Lys Gln Glu Cys Leu Arg Ala Cys Lys Lys Gly Phe Ile Gln Arg Ile Ser Lys Gly Gly Leu Ile Lys Thr Lys Arg Lys 286

991  AGA AAG AAG CAG AGA GTG AAA ATA GCA TAT GAA GCA ATT TTT GTT GAA GAA ATT TGA AAA AAT ATG TGA                                 304
     Arg Lys Lys Gln Arg Val Lys Ile Ala Tyr Glu Ala Ile Phe Val Glu Glu Ile Phe Val Lys Asn Met End

1081 AAT ATT TTA TAT GAA ATG TTT CAC TAT TTT CTA TTT CTA TTT CTC TAA AAT CGT TTT AAT TAA TAT CAT TAA ATT TTC TAT GCT TAT

1171 TGT ACT TGT TAT CAA CAC GTT TGT ATC AGA GTT GCT TTT CTA ATC TTG TTA AAT TGC TTA TTC TAC GTC TGT AAT TTA ACT GGC TAC

1261 TGG GAA ATT ACT TAT TTT CTG GAT CTA TCT CTA TCT TCA TTT AAC TAC AAA TTA TCA TAC TAC CGG CTA CAT CAA ATC AGT CCT TTG ATT

1351 CCA TTT GGT GAC CAT CTG TTT GAG AAT ATG ATC ATG TAA ATG ATT ATC TCC TTT ATA GCC TGT AAC CAG ATT AAG CCC CCC
```

FIG.3B

```
                                                                                                                    50
1      PSLFNRDPPI PAAQRPDFCL EPPYTGPCKA RIIRYFYNAK AGLCQTFVYG GCRAKRNNFK SAEDCMRTCG GAIGPMCKTG GRAEGEGKG
2                 FQTPPDLCQ LPQARGPCKA ALLRYFYBST SNACEPFTYG GCCGGNBNFE TTEMCLRICE PPQQTDKS
3                 TERPDFCL  EPPYTGPCKA AMIRYFYNAK AGFCETFVYG GCRAKSNNFK SAEDCMRTCG GA
4                 QGRPSFCN  LPAETGPCKA SFRQYYNSK  SGGCQQFIYG GCRGNQNRFD TTQQQCGVCV
5                 QGDKRDICR LPPEQGPCKG RIPRYFYNPA SRMCESFIYG GCKGNKNNFK TKAECVRACR PPERPGVCPK TSGPGICLHG
6                 QDHPKFCY  LPADPGRCKA HIPRFYYDSA SNKCNKFIYG GCPGNANNFK TWDECRQTCG ASA
7                 RPDFCE    LPAETGLCKA YIRSFHYNLA AQQCLQFIYG GCCGNANRFK TIDECRRTCV G
8                 RPRFCE    LPAETGLCKA RIRSFHYNRA AQQCLEFIYG GCCGNANRFK TIDECHRTCV G
9                 HDRPTFCN  LAPESGRCRG HLRRIYYNLE SNKCKVFFYG GCCGNANNFE TRDECRETCG GK
10                RDRPKFCY  LPADPGRCLA YMPRFYYNPA SNKCEKFIYG GCRCNANNFK TWDECRHTCV ASGIQPR
11                QPRRKLCI  LHRNPGRCYD KIPAFYYNQK KKQCERFDWS GCGGNSNRFK TIEECRRTICI G
12                RPYACE    LIVAAGPCMF FISAFYYSKG ANKCYPFTYS GCRGNANRFK TIEECRRTCV V
13                LQHRTFCK  LPAEPGPCKA SIPAFYYMWA AKKCQLFHYG GCKGNANRFS TIEKCRHACV G
14                QPLRKLCI  LHRNPGRCYQ KIPAFYYNQK KKQCZGFTWS GCCGNSNRFK TIEECRRTCI RK
15                AAKYCK    LPLRIGPCKR KIPSFYYKWK AKQCLPFDYS GCCGNANRFK TIEECRRTCV G
16                RQRHRDCD  KPPDKGNC.G PVRAFYDTR  LKTCKAFQYR GCCDHGNFK  SDHLCRCECE LY
17                RQRHRDCD  KPPDKGNC.G PVRAFYDTR  LKTCKAFQYR GCDDHGNFK  TETLCRCECL VYP
18                RKRHPDCD  KPPDTKIC.Q TVRAFYYKPS AKRCVQFRYG GCCDHGNFK  SDHLCRECE  LYR
19(1)             KEDSCQ    LDHAQGPCLG MISRYFYNGT SMACETFQYG GCLGNGNNFA SQKECLQTCR T
19(2)             VAACN     LPIVQGPCRA FIRLWAFDAA QQKCVLFTYG GCRGNGNKFY SQKECKEYCG IPGDGDEELL R
20(1)             KEDSCQ    LGYSQGPCLG MIKRYFYNGS SMACETFHYG GCMCGNMNFV SQKECLQTCR T
20(2)             VSACS     LPIVQGPCRA FIRLWAFDAA QQKCVLFNYG GCCGNGNKFY SQKECKEYCG VPGEEDEELL R
21(1)             KADSCQ    LDYSQGPCLG LFKRYFYNGT SMACETFLYG GCMGNLNNFL SQKECLQTCR T
21(2)             VEACN     LPIVQGPCRA FIQLWAFDAV KGKCVRFSYG GCKGNGNKFY SQKECKEYCG IPCEADERLL R
22(1)             KEDSCQ    LGYSAGPCMG MTSRYFYNGT SMACETFQYG GCMGNMNFV  TEKECLQTCR T
22(2)             VAACN     LPIVRGPCRA FIQLWAFDAV KGKCVLFPYG GCCGNGNKFY SEKECREYCG VPGDGDEELL RFSN
23(1)             LKLMHSFCA FKADDGPCKA IMKRFFNIF  TRQCEEFIYG GCEGNQNRFE SLEECKKMCT RDNANRIIKT TL
23(2)             QQEKPDFCF LEEDPGICRG YITRYFYNNQ TKQCERFKYC GCLGMMNNFE TLEECKNICE DGPNGFQVDN YG
23(3)             EFHGPSWCL TPADRGLCRA NENRFYYNSV IGKCRPFKYS GCCGNENNFT SKQECLRACK KGFIQRISKG GL
Consensus         .........C........G.C.. ...........................GC......F.....GC......C........F. ....C....C.
```

FIG.6

HUMAN TISSUE FACTOR INHIBITOR

This is a Continuation of application Ser. No. 07/566,280 filed Aug. 13, 1990, now abandoned, which is a Division of application Ser. No. 07/123,753, filed Nov. 23, 1987, which in turn is a continuation-in-part of application Ser. No. 07/077,366, filed Jul. 23, 1987, now abandoned.

BACKGROUND OF THE INVENTION

This invention relates to a coagulation inhibitor known as tissue factor inhibitor (TFI) and alternatively as lipoprotein associated coagulation inhibitor (LACI). More particularly, the invention relates to a cDNA clone representing essentially the full size TFI.

The coagulation cascade that occurs in mammalian blood comprises two distinct systems—the so-called intrinsic and extrinsic systems. The latter system is activated by exposure of blood to tissue thromboplastin (Factor III), hereinafter referred to as tissue factor (TF). Tissue factor is a lipoprotein that arises in the plasma membrane of many cell types and in which the brain and lung are particularly rich. Upon coming into contact with TF, plasma Factor VII or its activated form, Factor $VII_a$, forms a calcium-dependent complex with TF and then proteolytically activates Factor X to Factor $X_a$, and Factor IX to Factor $IX_a$.

Early studies concerning the regulation of TF-initiated coagulation showed that incubation of TF (in crude tissue thromboplastin preparations) with serum inhibited its activity in vitro and prevented its lethal effect when it was infused into mice. Extensive studies by Hjort, *Scand. J. Clin. Lab. Invest.* 9, Suppl. 27, 76–97 (1957), confirmed and extended previous work in the area, and led to the conclusion that an inhibitory moiety in serum recognized the Factor VII-TF complex. Consistent with this hypothesis are the facts that the inhibition of TF that occurs in plasma requires the presence of $Ca^{2+}$ (which is also necessary for the binding of Factor VII/$VII_a$ to TF) and that inhibition can be prevented and/or reversed by chelation of divalent cations with EDTA. More recent investigations have shown that not only Factor $VII_a$ but also catalytically active Factor $X_a$ and an additional factor are required for the generation of TF inhibition in plasma or serum. See Broze and Miletich, *Blood* 69, 150–155 (1987), and Sanders et al., *Ibid.*, 66, 204–212 (1985). This additional factor, defined herein as tissue factor inhibitor (TFI), and alternatively as lipoprotein associated coagulation inhibitor (LACI), is present in barium-absorbed plasma and appears to be associated with lipoproteins, since TFI functional activity segregates with the lipoprotein fraction that floats when serum is centrifuged at a density of 1.21 g/cm$^3$. According to Broze and Miletich, Supra, and *Proc. Natl. Acad. Sci. USA* 84, 1886–1890 (1987), HepG2 cells (a human hepatoma cell line) secrete an inhibitory moiety with the same characteristics as the TFI present in plasma.

In copending application Ser. No. 77,366, filed Jul. 23, 1987, now abandoned a purified tissue factor inhibitor (TFI) is disclosed which was secreted from HepG2 cells. It was found to exist in two forms, a $TFI_1$, migrating at about 37–40,000 daltons and a $TFI_2$ at about 25–26,000 daltons, as determined by sodium dodecylsulfate polyacrylamide gel electrophoresis (SDS-PAGE). A partial N-terminal amino acid sequence for the TFI was assigned as:

```
1                                                    15
X—X—Glu—Glu—Asp—Glu—Glu—His—Thr—Ile—Ile—Thr—Asp—Thr—Glu—

16                                          27
Leu—Pro—Pro—Leu—Lys—Leu—Met—His—Ser—Phe—(Phe)—Ala
``` wherein X-X had not been determined. The disclosure of said application is incorporated herein by reference.

BRIEF DESCRIPTION OF THE INVENTION

In accordance with the present invention, the complete coding sequence of a cDNA clone representing essentially the full size tissue factor inhibitor (TFI) has been developed.

Initially, human placental and fetal liver λgt11 cDNA libraries were screened with a rabbit polyclonal antiserum raised against a purified TFI. Immunologically positive clones were further screened for $^{125}$I-Factor $X_a$ binding activity. Seven clones were obtained which were immunologically and functionally active. The longest clone, placental-derived λP 9, was 1.4 kilobases (kb) long while the other six were 1.0 kb in length. Partial DNA sequencing showed the 1.0 kb clones to have sequences identical to part of the longer 1.4 kb clone. Nucleotide sequence analysis showed that λP9 consisted of a 1432 basepair (bp) cDNA insert that includes a 5'-noncoding region of 133 bp, an open reading frame of 912 bp, a stop codon, and a 3'-noncoding region of 384 bp.

The cDNA sequence encodes a 31,950 Dalton protein of 276 amino acids which includes 18 cysteines and 7 methionines. The translated amino acid sequence shows that a signal peptide of about 28 amino acids precedes the mature TFI protein. It will be understood that the "mature" TFI is defined to include both TFI and methionyl TFI by virtue of the ATG translational codon in the λP9 clone described herein.

There are three potential N-linked glycosylation sites in the TFI protein with the sequence Asn-X-Ser/Thr, wherein X can be any of the common 20 amino acids. These sites are at amino acid positions Asn 145, Asn 195, and Asn 256, when the first methionine after the 5'-noncoding region is assigned amino acid position +1.

The translated amino acid sequence of TFI shows several discernible domains, including a highly negatively charged N-terminal, a highly positively charged carboxy-terminal, and an intervening portion consisting of 3 homologous domains with sequences typical of Kunitz-type enzyme inhibitors. Based on a homology study, TFI appears to be a member of the basic protease inhibitor gene superfamily.

The original source of the protein material for developing the cDNA clone λP9 was human placental tissue. Such tissue is widely available after delivery by conventional surgical procedures. The λgt11 (lac5 nin5 c1857 S100) used herein is a well-known and commonly available lambda phage expression vector. Its construction and restriction endonuclease map is described by Young and Davis, *Proc. Natl. Acad. Sci. USA* 80, 1194–1198 (1983).

Northern blot analysis showed that the following liver-derived cell lines: Chang liver, HepG2 hepatoma, and SK- HEP-1 hepatoma, all contained 2 major species of mRNA (1.4 and 4.4 kb) which hybridized with the TFI cDNA.

The cloning of the cDNA for TFI and development of its entire protein sequence and structural domains as disclosed herein permits detailed structure-functional analyses and provides a foundation for study of its biosynthetic regulations. The invention thus is important to medical science in the study of the coagulation cascade with respect to agents which are able to inhibit Factor $X_a$ and Factor $VII_a$/TF enzymatic complex.

The novel TFI of this invention has been isolated in essentially pure form apart from its naturally occuring admixtures.

DETAILED DESCRIPTION OF THE INVENTION

Figure 1:
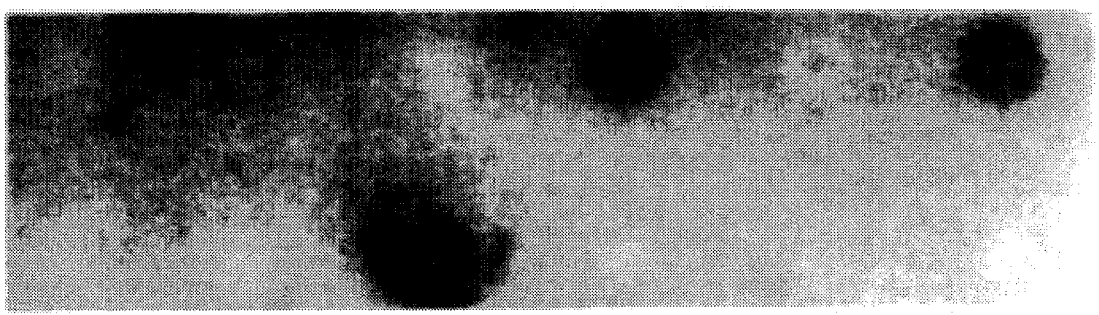

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which:

FIG. 1 shows the screening of λgt11 clones with $^{125}$I-Factor $X_a$. Cloned phage lysates (0.1 ml) were spotted on a nitrocellulose paper by suction using a dot blot apparatus. The nitrocellulose paper was then probed with $^{125}$I-Factor $X_a$ and autoradiographed as described hereinafter. The clones that appear as dark spots are positive clones that bind $^{125}$I-Factor $X_a$. Control λgt11 (lower right corner) and other clones do not bind $^{125}$I-Factor $X_a$.

Figure 2:
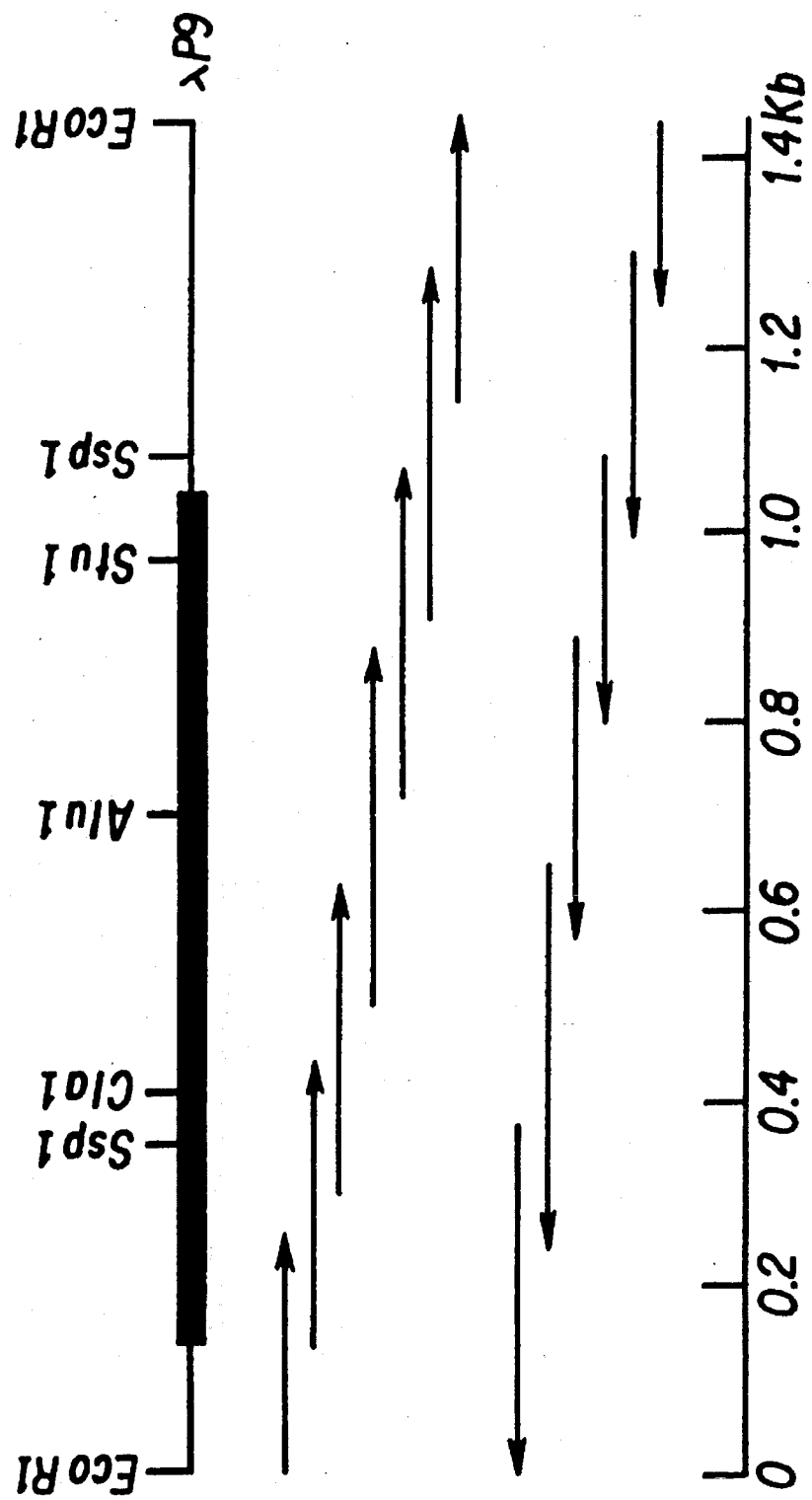

FIG. 2 shows a partial restriction map and sequencing strategy for the λP9 inserts. The scale at the bottom indicates the nucleotide position. The thick bar represents the coding region. The thin bars represent 5'- and 3'-noncoding regions. The restriction endonuclease sites were confirmed by digestion. The arrows show the overlapping M13 clones used to sequence the cDNA.

FIG. 3 shows the nucleotide sequence and translated amino acid sequence of the human TFI cDNA. Nucleotides are numbered on the left and amino acids on the right. The underlined sequences have been independently confirmed by amino acid sequence analysis of the purified TFI protein and two $V_8$ protease + trypsin digested peptides. Amino acid + 1 was assigned to the first methionine after a stop codon of the 5'-noncoding region. Potential N-lined glycosylation sites are marked by asterisks.

Figure 4:
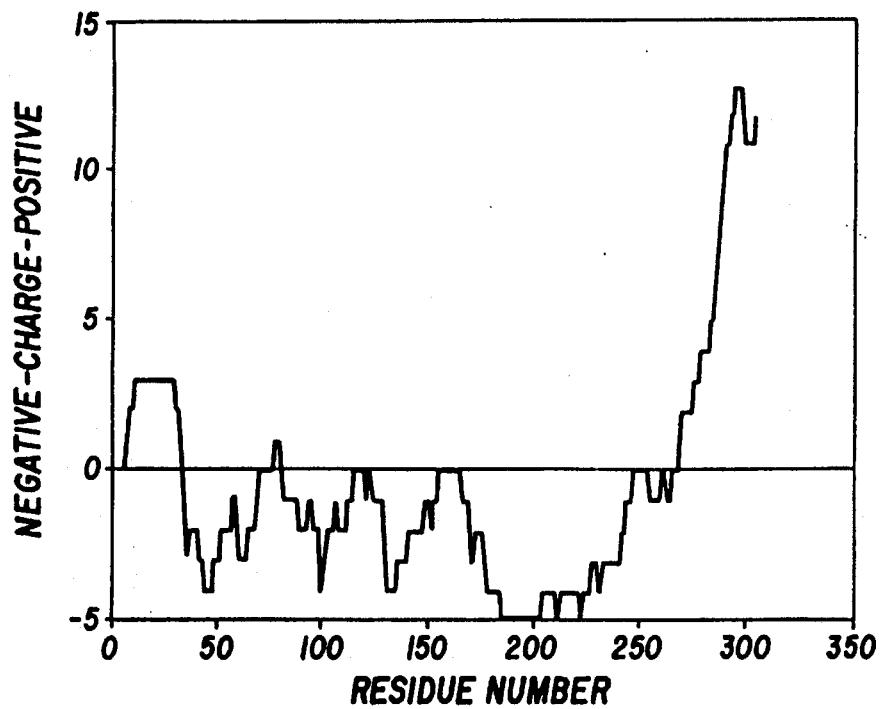

FIG. 4 is a graphical representation which shows the charge distribution of the amino acid sequence in TFI. Charges are calculated from the first residue to the i-th residues and displayed at the i-th residue. Thus the value of the i-th position is the summation of all charges from the first residue to the i-th residue and the difference of the charges between the i-th and j-th residue (j>i) is the net charge of the fragment from i-th to j-th residue.

Figure 5:
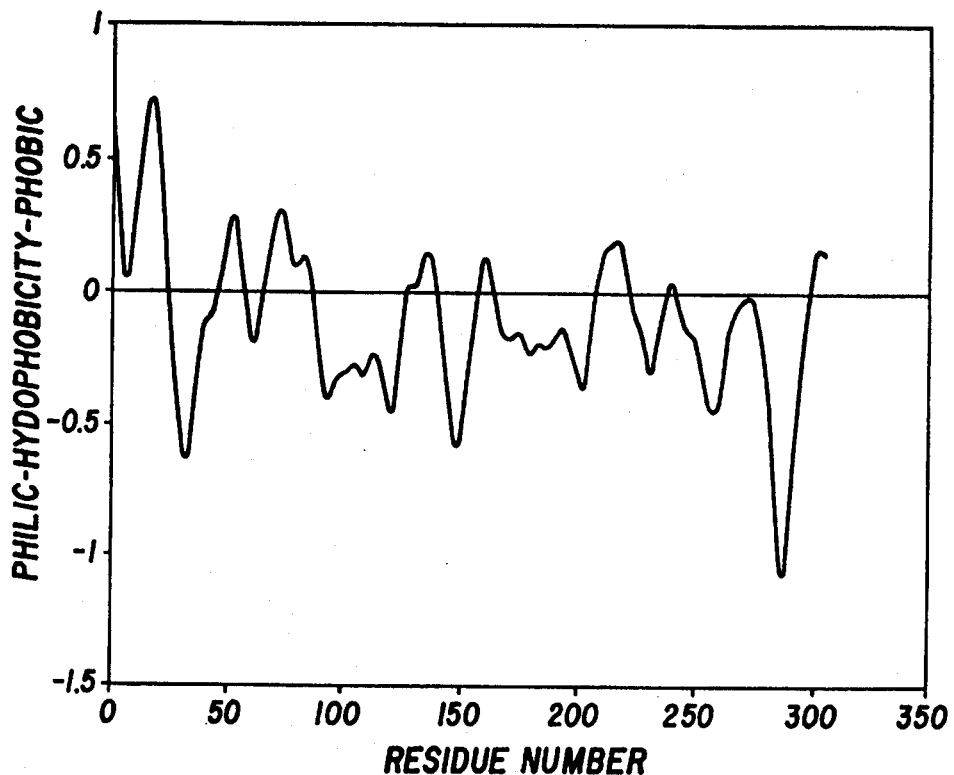

FIG. 5 is a graphical representation which shows the hydrophobicity profile of TFI. The hydrophobicity profile was analyzed by a computer program whereby the hydrophobicity index of the amino acid residues is defined as the depth to which an amino acid residue is buried inside a protein (from X-ray crystallographic data) [Kidera et al., *J. Protein Chem.* 4, 23–55 (1985)]. The hydrophobicity profile along the sequence was smoothed using the program ICSSCU in IMSL LIbrary [IMSL Library Reference Manual, 9th ed., Institute for Mathematical and Statistical Subroutine Library, Houston, Tex. (1982)].

FIG. 6 shows an alignment of the basic protease inhibitor domains of TFI with other basic protease inhibitors. All the sequences except TFI were obtained from the National Biomedical Research Foundation Protein Sequence Database (Georgetown University, Washington, D.C., release 13, Jun. 1987). 1. Bovine basic protease inhibitor precursor; 2. Bovine colostrum trypsin inhibitor; 3. Bovine serum basic protease inhibitor; 4. Edible snail isoinhibitor K; 5. Red sea turtle basic protease inhibitor (only amino acids 1–79 presented); 6. Western sand viper venom basic protease inhibitor I; 7. Ringhals venom basic protease inhibitor II; 8. Cape cobra venom basic protease inhibitor II; 9. Russell's viper venom basic protease inhibitor II; 10. Sand viper venom basic protease inhibitor III; 11. Eastern green mamba venom basic protease inhibitor I homolog; 12. Black mamba venom basic protease inhibitor B; 13. Black mamba venom basic protease inhibitor E; 14. Black mamba venom basic protease inhibitor I; 15. Black mamba venom basic protease inhibitor K; 16. β-1-Bungarotoxin B chain (minor); 17. β-1-Bungarotoxin B chain (major); 18. β-2-Bungarotoxin B chain; 19. Horse inter-α-trypsin inhibitor [ amino acids 1–57(1); 58–123 (2)]; 20. Pig inter-α-trypsin inhibitor [ amino acids 1–57(1); 58–123(2)]; 21. Bovine inter-α-trypsin inhibitor [ amino acids 1–57(1); 58–123(2)]; 22. Human α-1-microglobulin/inter-α-trypsin inhibitor precursor [amino acids 227–283(1); 284–352(2)]; 23. TFI [ amino acids 47–117(1); 118–188(2); 210–280(3)]. Gaps were included in 16, 17, 18 to achieve best alignment. Standard one letter codes for amino acids are used.

Figure 7:
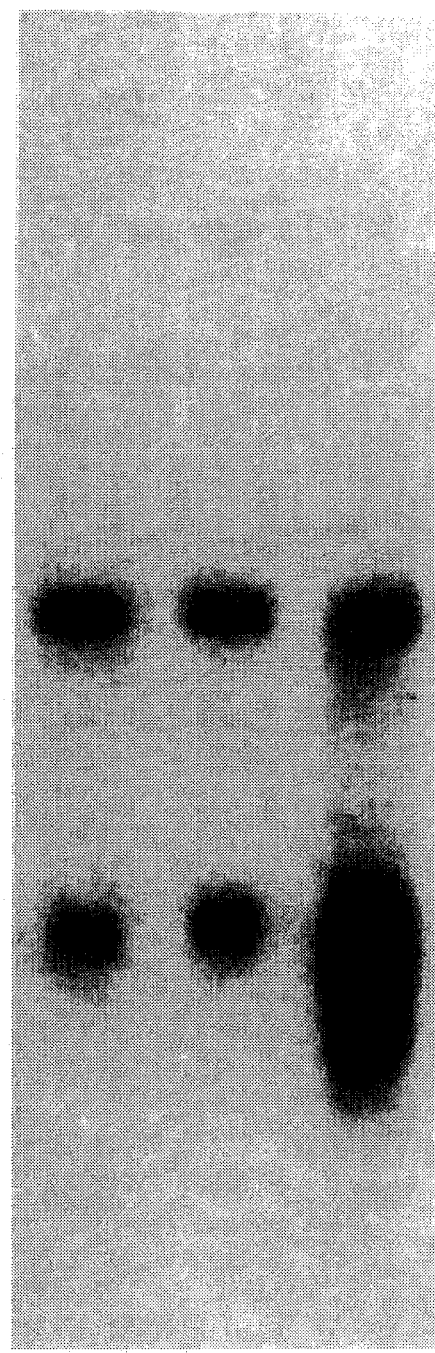

FIG. 7 shows the Northern blot analysis of RNAs from 3 liver-derived cell lines. Ten μg of poly(A)$^+$ RNA were used per lane. Lane 1, Chang liver cell; lane 2, SK-HEP-1 hepatoma cell; lane 3, HepG2 hepatoma cell.

Figure 8A:
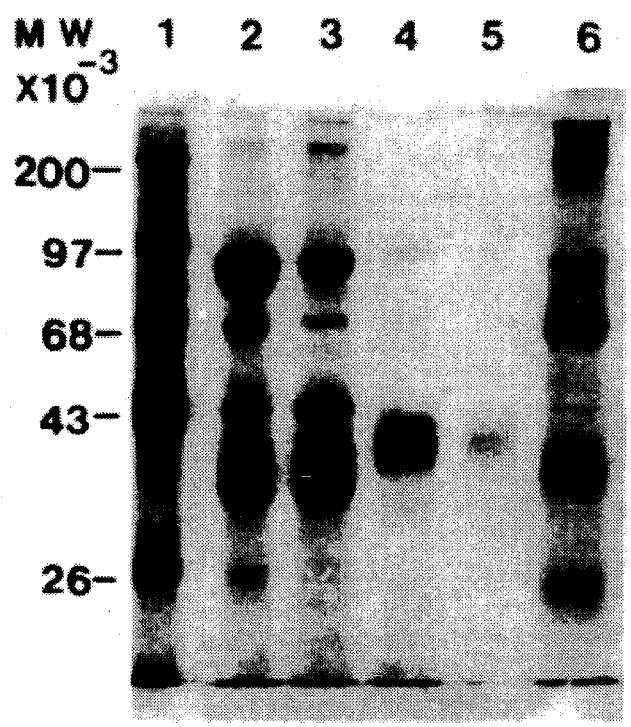

FIG. 8A shows the SDS-PAGE of TFI isolated from Chang liver cells (lane 2), SK-HEP-1 (lanes 3 and 4), and HepG2 cells (lanes 5 and 6) by immunoaffinity chromatography in further embodiments of the invention, with standard molecular weight markers shown in lane 1.

Figure 8B:
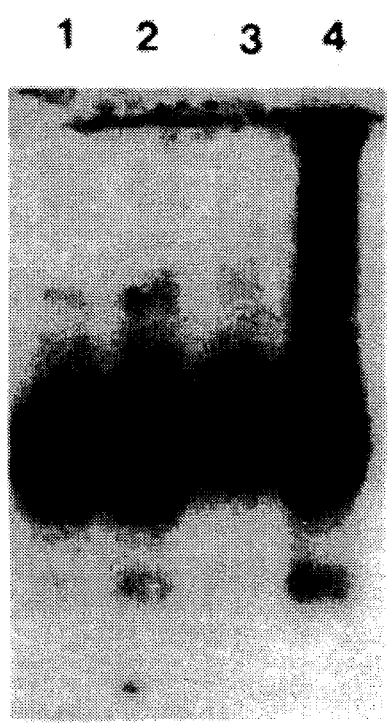

FIG. 8B shows the Western Blotting (electrophoretic transfer) on nitrocellulose paper and staining with $^{125}$I-$X_a$ followed by autoradiography of electrophoretically separated proteins from lanes 2, 3, 4 and 6 of FIG. 8A in lanes 1, 2, 3 and 4, respectively.

Standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP). As is conventional for convenience in the structural representation of a DNA nucleotide sequence, only one strand is shown in which A on one strand connotes T on its complement and G connotes C. Amino acids are shown either by three letter or one letter abbreviations as follows:

| Abbreviated Designation | Amino Acid | |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |

| Abbreviated Designation | | Amino Acid |
| --- | --- | --- |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases described herein have the following restriction sequences and (indicated by arrows) cleavage patterns:

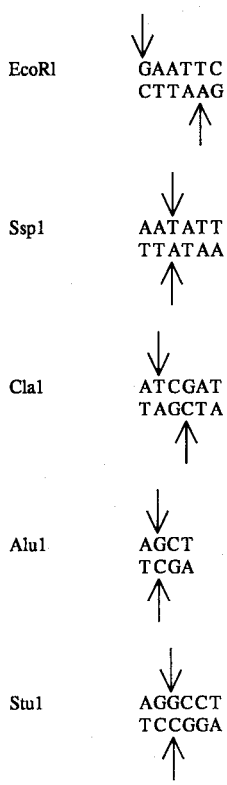

| | |
| --- | --- |
| EcoRl | GAATTC / CTTAAG |
| Sspl | AATATT / TTATAA |
| Clal | ATCGAT / TAGCTA |
| AluI | AGCT / TCGA |
| StuI | AGGCCT / TCCGGA |

In order to illustrate specific preferred embodiments of the invention in greater detail, the following exemplary laboratory preparative work was carried out.

EXAMPLE 1

Materials

Human placental and fetal liver cDNA libraries were obtained from Clonetech. The protoblot immunoscreening kit was purchased from Promega Biotech. Restriction enzymes were from New England Biolabs. Calf intestine alkaline phosphatase, T4 DNA ligase, DNA polymerase I (Klenow), exonuclease III and S1 nuclease were from Boehringer Mannheim. dNTPs were from P.L. Biochemicals. 5'-[α-$^{35}$S]-thio-dATP (600 Ci/mmol) was from Amersham. Sequencing kit (Sequenase) was from United States Biochemicals. Chang liver cells (ATCC CCL 13) and HepG2 hepatoma cells (ATCC HB 8065) were obtained from the American Type Culture Collection. SK-HEP-1 hepatoma cells were originally derived from a liver adenocarcinoma by G. Trempe of Sloan-Kettering Institute for Cancer Research in 1971 and are now widely and readily available.

$^{125}$I-Factor $X_a$ was prepared by radio-labeling using Iodogen. The specific activity was 2000 dpm/ng. Greater than 97% of radioactivity was precipitable with 10% trichloroacetic acid (TCA). The iodinated protein retained >80% of their catalytic activity toward Spectrozyme $X_a$ (American Diagnostica product).

An anti-TFI-Ig Sepharose® 4B column was prepared as follows: A peptide (called TFI-peptide) containing a sequence corresponding to the amino acid sequence 3–25 of the mature TFI was synthesized using Biosystem's solid phase peptide synthesis system. The TFI-peptide (5 mg) was conjugated to 10 mg of Keyhole lympet hemocyanin by glutaraldehyde. Two New Zealand white rabbits were each immunized by intradermal injection with a homogenate containing 1 ml of Freund complete adjuvant and 1 ml of conjugate (200 µg of TFI-peptide). One month later the rabbits were each boosted with a homogenate containing 1 ml of Freund incomplete adjuvant and 1 ml of conjugate (100 µg of conjugate). Antiserum was collected each week for 3 months and booster injections were performed monthly. To isolate specific antibody against TFI-peptide, the antiserum was chromatographed on a TFI-peptide Sepharose 4B column. The column was washed with 10 volumes of PBS (0.4M NaCl-0.1M benzamidine-1% Triton® X-100) and the same solution without Triton X-100. The antibody was eluted with 0.1M glycine/HCl, pH 2.2, immediately neutralized by adding 1/10 volume of 1M Tris-OH and dialyzed against saline solution. The isolated antibody was coupled to cyanogen bromide activated Sepharose 4B by the manufacturer's (Pharmacia) method and used to isolate TFI from the cell culture medium.

Chang liver cell was cultured by the method described previously by Broze and Miletich, *Proc. Natl. Acad. Sci. USA* 84, 1886–1890 (1987). The conditioned medium was chromatographed on the anti-TFI-Ig Sepharose 4B column. The column was washed with 10 volumes of PBS-1% Triton X-100 and PBS. The bound TFI was eluted with 0.1M glycine/HCl, pH 2.2. The immunoaffinity isolated TFI was further purified by preparative sodium dodecylsulfate polyacrylamide gel electrophoresis (Savant apparatus). Amino acid analysis of the final product showed the same amino terminal sequence as the TFI isolated from HepG2 cells as described in copending application, Ser. No. 77,366, filed Jul. 23, 1987. The isolated Chang liver TFI was then used to immunize rabbits by the immunization protocol described above. The antiserum obtained had a titer of about 100 µg/ml in the double immunodiffusion test. This antiserum was used in the immuno-screening of λgt11 cDNA libraries.

Methods

Isolation of cDNA clones.

Methods for screening the placental and fetal liver cDNA libraries with antibody, plaque purification, and preparation of λ-phage lysate and DNA were as described by Wun and Kretzmer, *FEBS Lett.* 1, 11–16 (1987). The antiserum was pre-adsorbed with BNN97 λgt11 lysate and diluted 1/500 for screening the library.

Screening of factor $X_a$ binding activity

Recombinant proteins induced by isopropyl-β-thiogalactoside from immuno-positive λ-phage isolates or from control λgt11 were screened for Factor $X_a$ binding activity. The λ-phage lysates (0.1 ml) were filtered through a nitrocellulose paper using a dot-blot apparatus (Bio Rad). The nitrocellulose paper was then immersed and agitated in a phosphate buffered saline containing 5 mg/ml bovine serum albumin and 2.5 mg/ml bovine gamma globulin at room temperature for 1 h. The solution was replaced with $^{125}$I-Factor $X_a$ (1.0×10$^6$ cpm/ml) dissolved in the same solution supplemented with 0.1 mg/ml heparin and the agitation continued for another hour. The nitrocellulose paper was then washed with phosphate buffered saline containing 0.05% Tween® 20. The washing buffer was changed every 5 min., 4 times. The nitrocellulose paper was then air-dryed and prepared for autoradiography using Kodak XR5 film. The film was developed after 1 week exposure.

Preparation of poly(A)$^+$ RNA and Northern blotting.

Total RNAs were prepared from cultured Chang liver cell, HepG2 hepatoma cell and SK-HEP-1 hepatoma cell using the sodium perchlorate extraction method of Lizardi, and Engelberg, *Anal. Biochem.* 98, 116–122, (1979). Poly(A)$^+$ RNAs were isolated by batch-wise adsorption on oligo(dT)-cellulose (P-L Biochemical, type 77F) using the procedure recommended by the manufacturer. For Northern blot analysis, 10 μg each of poly(A)$^+$ RNA was treated with glyoxal [Thomas, *Methods Enzymol.* 100, 255– 266 (1983)] and subjected to agarose gel electrophoresis in a buffer containing 10 mM sodium phosphate, pH 7.0. Bethesda Research Laboratory's RNA ladder was used as a molecular weight marker. The RNAs were transblotted onto a nitrocellulose paper which was then baked at 80° for 2 h. The insert DNA of λP9 clone was radiolabeled with $^{32}$P by nick translation and used as a probe [Maniatis et al., *Molecular Cloning: A Laboratory Model*, Cold Spring Laboratory, Cold Spring Harbor, N.Y., (1982)]. The blot was hybridized with 5×10$^6$ cpm of the probe in 5 ml of a solution containing 50% formamide, 5X SSC, 50 mM sodium phosphate, pH 7.0, 250 μg/ml denatured salmon sperm DNA, and 1X Denhardt's solution at 42° for 16 h. The filter was washed in 0.1% sodium dodecylsulfate (SDS), 2X SSC at room temperature 3 times, each time 5 min., and in 0.1% SDS, 0.2×SSC at 50° twice, each 5 min. The nitrocellulose paper was then air dried, autoradiographed for 3 days at −70° using Kodak XAR-5 film and intensifying screen.

Other recombinant DNA methods.

Preparation of cloned λgt11 DNA, subcloning in pUC19 plasmid and M13mp18 vector, generation of deletion by exonuclease III digestion and DNA sequencing by dideoxy method [Sanger et al., *Proc. Natl. Acad. Sci. USA* 83, 6776–6780 (1977)], were performed as described by Wun and Kretzmer, supra.

The program FASTP written by Lipman and Pearson, *Science* 227 1435–1441 (1985), was used to identify homologous families of proteins from National Biomedical Research Foundation Sequence Data Bank (release 13, Jun. 1987) and to align the sequences within the homologous family.

RESULTS

Screening of cDNA libraries

A number of cell lines were screened for the presence of TFI in the conditioned media and it was found that several liver-derived cell lines, Chang liver, HepG2 hepatoma, and SK-HEP-1 hepatoma secrete TFI in culture. Initially, an antiserum against TFI was used to screen a human fetal liver λgt11 cDNA library (10$^6$ plaque forming units), and 15 immunologically positive clones were obtained. Subsequently, the same method was used to screen a placental λgt11 cDNA library. Out of 10$^6$ plaque forming units, 10 immunologically positive clones were obtained. These clones were plaque purified and the lysates of the purified clones were tested for the functional activity of TFI. The isopropylthio-galactoside induced phage lysates were absorbed on the nitrocellulose paper and screened for the $^{125}$I-Factor $X_a$ binding activity. FIG. 1 demonstrates that some of these immunologically positive clones showed the ability to bind the $^{125}$I-Factor $X_a$ on the nitrocellulose paper. In all, 3 out of 15 immunologically positive fetal liver clones, and 4 out of 10 immunologically positive placental clones showed $^{125}$I-Factor $X_a$ binding activity. These immunologically and functionally positive clones were digested with EcoR1 and the size of the inserts were estimated by gel electrophoresis. One clone from placental library (λP9) had an insert of approximately 1.4 kb, while all the other clones contain inserts of approximately 1.0 kb. Partial DNA sequencing has shown that 1.0 kb clones contain sequences identical to part of the longer 1.4 kb placental clone (λP9). The λP9 was therefore selected for complete sequencing.

Nucleotide sequence and predicted protein sequence of TFI cDNA isolate

The λP9 clone was subjected to restriction mapping, M13 subcloning and sequencing by the strategy shown in FIG. 2. The entire sequence was determined on both strands by the exonuclease III deletion method [Henikoff, *Gene* 28, 351–359 (1984)] and found to consist of 1432 bases in length. The sequence is shown in FIG. 3. It contains a 5'-noncoding region of 133 bases, an open reading frame of 912 nucleotides, and a 3'-noncoding region of 387 nucleotides. The first ATG occurs at nucleotide 134 in the sequence TAGATGA which was closely followed by a second ATG at nucleotide 146 in the sequence ACAATGA. These are possibly the initiation sequences, although they differ from the proposed consensus sequence for initiation by eukaryotic ribosome, ACCATGG [Kozak, *Cell* 44, 283–292 (1986)]. Twenty-eight amino acids precede a sequence corresponding to the N-terminal of the mature protein. The length and composition of the hydrophobic segment of these 28 amino acids are typical of signal sequences [Von Heijne, *Eur. J. Biochem.* 133, 17–21 (1983); *J. Mol. Biol.* 184, 99–105 (1985)]. A signal peptidase possibly cleaves at Ala$_{28}$–Asp$_{29}$ to give rise to a mature protein. The sequence predicted for mature TFI consists of 276 amino acids that contains 18 cysteine residues and 7 methionines. The calculated mass of 31,950 Daltons based on the deduced protein sequence for mature TFI is somewhat lower than the 37–40 kDa estimated by sodium dodecyl sulfate polyacrylamide gel electrophoresis of isolated protein, and the difference probably reflects the contribution of glycosylation to the mobility of the natural protein. The deduced protein sequence corresponding to the mature protein contains 3 potential N-linked glycosylation sites with the sequence Asn-X-Thr/Ser (amino acid positions 145, 195, and 256). Amino acid sequence analysis of purified whole TFI and two isolated proteolytic fragments match exactly the protein sequence deduced from cDNA sequence (FIG. 3, underlined), indicating the isolated cDNA clone encodes TFI. The 3'-noncoding region is A+T rich (70% A+T). Neither consensus polyadenylation signal, AATAAA [Proudfoot and Brownlee, *Nature* 252, 359–362 (1981)] nor the poly A tail was found in this clone, possibly due to artefactual loss of part of 3' terminal portion during construction of the library.

Charge distribution, hydrophobicity/hydrophilicity, and internal homology

The translated amino acid sequence of the TFI contains 27 lysines, 17 arginines, 11 aspartic acids, and 25 glutamic acids. The charge distribution along the protein is highly uneven as shown in FIG. 4. The signal peptide region contains 2 positively charged lysine with 26 neutral residues. The amino-terminal region of the mature protein contains a highly negatively charged stretch. Six of the first 7 residues are either aspartic acid or glutamic acid which are followed closely by two more negatively charged amino acids downstream before a positively charged lysine residue appears. The center portion of the molecule is generally negatively charged. At the carboxy terminal, there is a highly positively charged segment. The amino acids 265 to 293 of TFI contain 14 positively charged amino acids including a 6-consecutive arginine + lysine residues.

The predicted hydrophilicity/hydrophobicity profile of TFI protein is shown in FIG. 5. The signal peptide contains a highly hydrophobic region as expected. The rest of the molecule appears rather hydrophilic.

The translated amino acid sequence of TFI contains several discernible domains. Besides the highly negatively charged N-terminal domain and the highly positively charged C-terminal domain, the center portion consists of 3 homologous domains which have the typical sequences of the Kunitz-type inhibitors (see below).

Homology to other proteins

By searching the National Biomedical Research Foundation sequence data base, it was found that the N-terminal domain and C-terminal domain of TFI do not show significant homology to other known proteins. The 3 internal homologous domains, however, are each homologous to the sequences of other basic protease inhibitors including bovine pancreatic basic protease inhibitor (aprotinin), venom basic protease inhibitors, and inter-α-trypsin inhibitors (FIG. 6). It is noteworthy that disulfide bonding structure is highly conserved in all these inhibitors. Based on these homologies, it is clear that TFI belongs to the basic protease inhibitor gene superfamily.

Northern blotting

Poly(A)+ RNAs were purified from TFI-producing liver-derived cell lines, Chang liver, HepG2 hepatoma, and SK-HEP-1 hepatoma cells. The poly (A)+ RNAs were resolved by denaturing agarose gel electrophoresis, transblotted onto a nitrocellulose paper and probed with $^{32}$P-labeled TFI cDNA (λP9). As shown in FIG. 7, two major bands of hybridization were observed that corresponded to mRNAs of 1.4 kb and 4.4 kb in all three cell lines tested. Several other cell lines were tested which do not produce detectable amounts of TFI and in which no hybridization with the probe was found. (data not shown).

Various other examples will be apparent to the person skilled in the art after reading the present disclosure without departing from the spirit and scope of the invention. It is intended that all such further examples be included within the scope of the appended claims.

EXAMPLE 2

Isolation of TFI from several cell sources, namely Chang Liver cells, SK-HEP-1 cells, and HepG2 cells was carried out by immunoaffinity chromatography using as the immunogen a synthetic peptide having an amino acid sequence 3–25 of the mature TFI described hereinbefore as follows:

Immunization

A TFI-peptide containing a sequence corresponding to the amino acid sequence 3-25 of the mature TFI was synthesized using Biosystem's solid phase peptide synthesis. The TFI-peptide (5 mg) was conjugated to 10 mg of Keyhole lympet hemocyanin by glutaraldehyde. Two New Zealand white rabbits were each immunized by intradermal injection with a homogenate containing 1 ml of Freund complete adjuvant and 1 ml of the conjugate (200 μg of TFI-peptide). One month later,, the rabbits were each boosted with a homogenate containing 1 ml of Freund incomplete adjuvant and 1 ml of the conjugate (100 μg of TFI-peptide). Antiserum was collected each week thereafter. Booster injection was performed monthly until the rabbits were exsanguinated after 3 months.

Isolation of anti-TFI-peptide-Iq

The synthetic TFI-peptide (3 mg) was coupled to 0.8 g of CNBr-activated Sepharose® 4B using the manufacturer's published procedure (Pharmacia). To isolate specific antibody, pooled antiserum (15 ml) was mixed with equal volume of a solution (PNBT) containing PBS, 0.4M NaCl, 0.1M benzamidine and 1% Triton® X-100 and chromatographed on the TFI-peptide Sepharose 4B column at room temperature. The column was washed with 30 PNBT solution and then with the same solution without Triton X-100. The bound antibody was eluted with 0.1 M glycine/HCl, pH 2.2, immediately neutralized by adding 1/10 volume of 1M Tris-OH and extensively dialyzed against saline solution. Approximately 6.5 mg anti-TFI-peptide Ig was isolated from 15 ml of antiserum.

Cell Culture

Chang liver, SK hepatoma and HepG2 cells were grown to confluency in Dulbecco's Modified Eagle's Medium (DMEM) supplemented with 10% fetal bovine serum, 50 units/ml penicillin and 50 μg/ml streptomycin in 175-cm$^2$ flasks. Five flasks each of cells were trypsinized and used to seed one 10-chamber cell factory (Nunc). After confluency (~1 week), the cells were washed with PBS two times and incubated in a serum free medium. The serum free medium consisted of DMEM supplemented with 0.5% lactalbumin hydrolysate, 50 units/ml aprotinin, ITS premix (insulin-transferin-selenium, Collaborative Research product), 20 ng/ml liver cell growth factor (glycyl-histidyl-lysine) and 100 ng/ml phorbol 12-myristate 13-acetate. The serum free medium was replaced with fresh medium every 3 days. The cells can be maintained under these conditions for > 2 months. The pooled conditioned media were made 0.02% NaN$_3$ and 0.01% Triton X-100 and stored at 4°. Some media were concentrated 20 to 100 fold by ultrafiltration using Amicon's YM30 spiral membrane system.

Immunoaffinity purification of TFI

Isolated anti-TFI-peptide-Ig (20 mg) was coupled to 2 g of CNBR-activated Sepharose 4B by the manufacturer's published procedure. The bed volume of the gel was 7 ml. To isolated TFI, the conditioned media (unconcentrated or concentrated) from Chang liver, SK hepatoma or HepG2 cells were chromatographed on the anti-TFI-peptide-Ig Sepharose 4B column at a speed of 2 ml/min in the cold room, until significant TFI activity appeared in the flow through. The column was then wased with 70 ml of PNBT and 70 ml of the same solution without Triton X-100. The bound TFI were eluted with 0.1M glycine/HCl, pH 2.2, and concentrated to approximately 0.6 ml by vacuum dialysis against 0.1M glycine/HCl, pH 2.2.

Results:

By immunoaffinity chromatography on an anti-TFI-peptide-Ig Sepharose 4B column, TFI was isolated from a number of liver derived cell lines, Chang liver, SK hepatoma and HepG2 hepatoma. FIG. 8A shows the SDS-PAGE of the proteins eluted from the anti-TFI-peptide-Ig Sepharose column. In different preparations, one observes somewhat different protein profiles. In some preparations, a 40 kDa protein is the only major protein (lanes 4 and 5); in others, a number of protein bands coexist and a 38 kDa protein is a prominent band instead of the 40 kDa protein. To establish which proteins are TFI related, the $^{125}$I-X$_a$ binding study was performed. The isolated TFI samples were electrophoresed in a 12% SDS-polyacrylamide gel and the proteins were then electrophoretically transblotted onto a nitrocellulose paper and screened for $^{125}$I-X$_a$ binding activity. It was found that three major bands with apparent molecular weights of 40, 38, and 25 kDa possess $^{125}$I-X$_a$ binding activity while other bands are not. (FIG. 8B). Sequence analysis of the 38 kDa band from SK hepatoma cells shows that it possesses the same amino terminal sequence as the 40 kDa TFI isolated from HepG2 cells in Example 1, above. Based on the immunoaffinity, amino acid sequencing, and the $^{125}$I-X$_a$ binding studies, it appears that the 40, 38, and 25 kDa inhibitors may be derived from the same molecule.

The results of the above laboratory preparative work leading to the isolation of TFI from several cell sources by immunoaffinity chromatography are further exemplified by the following detailed description of FIGS. 8(A) and 8(B) of the drawings.

FIG. 8. This figure shows the SDS-PAGE of immunoaffinity isolated TFI and screening of $^{125}$I-X$_a$ binding activity. (A) SDS-PAGE. Electrophoresis was carried out on a 12% polyacrylamide gel. Lane 1, molecular weight markers; lane 2, Chang liver TFI; lane 3, SK hepatoma TFI (preparation 1); lane 4, SK hepatoma TFI (preparation 2); lane 5, HepG2 TFI (preparation 1); lane 6, HepG2 TFI (preparation 2). (B) Screening of $^{125}$I-X$_a$ binding activity. Samples were electrophoresed on a 12% polyacrylamide gel. The proteins were electrophoretically transblotted onto a nitrocellulose paper using Bio-Rad Trans-Blot® apparatus and procedure. After the transfer, the nitrocellulose paper was first gently shaken in PBB solution (PBS containing 5 mg/ml BSA and 2.5 mg/ml bovine gamma globulin) and then in PBB solution containing 400 ng/ml $^{125}$-I-X$_a$, each at room temperature for 1 hour. The nitrocellulose paper was then dried and autoradiographed for 3 days using Kodak XAR-5 film. Lane 1, Chang liver TFI; lane 2, SK hepatoma TFI (preparation-1); lane 3, SK hepatoma TFI (preparation 2); and lane 4, HepG2 TFI (preparation 2).

What is claimed is:

1. Human tissue factor inhibitor in essentially pure form apart from its naturally occurring admixtures and having the protein amino acid sequence as shown in FIG. 3 of the drawings.

2. The protein of claim 1 which is glycosylated.

* * * * *